United States Patent [19]

Clerici et al.

[11] 4,110,377

[45] Aug. 29, 1978

[54] PROCESS FOR THE ALKYLATION OF SECONDARY ALIPHATIC AMINES IN THE PRESENCE OF AN AMIDE OF A TRANSITION METAL

[75] Inventors: Mario Gabriele Clerici, San Donato Milanese (Milan); Federico Maspero, Milan; Alfonso D'Alfonso, San Donato Milanese (Milan), all of Italy

[73] Assignee: ANIC S.p.A., Italy

[21] Appl. No.: 831,241

[22] Filed: Sep. 7, 1977

[30] Foreign Application Priority Data

Oct. 28, 1976 [IT] Italy ............................. 28778 A/76

[51] Int. Cl.$^2$ .................... C07C 85/22; C07C 85/24
[52] U.S. Cl. ........................ 260/583 R; 252/431 N; 260/563 R; 260/563 C; 260/578
[58] Field of Search ............. 260/583 R; 252/431 N

[56] References Cited

U.S. PATENT DOCUMENTS

| 2,501,556 | 3/1950 | Whitman | 260/583 R X |
|---|---|---|---|
| 2,750,417 | 6/1956 | Closson et al. | 260/577 |
| 2,814,646 | 11/1957 | Kolka et al. | 252/431 N X |
| 3,420,864 | 1/1969 | Riess et al. | 252/431 N X |
| 3,691,095 | 9/1972 | Kroll et al. | 252/431 N X |
| 3,709,953 | 1/1973 | Bergem et al. | 252/431 N X |
| 3,794,604 | 2/1974 | Throckmorton et al. | 252/431 N X |
| 3,884,833 | 5/1975 | Wilke et al. | 252/431 N |
| 3,917,607 | 11/1975 | Normant | 260/583 R X |

FOREIGN PATENT DOCUMENTS 526,875 6/1956 Canada .......................... 260/583 R
2,117,970 10/1971 Fed. Rep. of Germany ...... 260/583 R

OTHER PUBLICATIONS

Lappert, "Chem. Ab.", Ab. No. 70:83813m (1969).

Primary Examiner—Winston A. Douglas
Assistant Examiner—John J. Doll
Attorney, Agent, or Firm—Morgan, Finnegan, Pine, Foley & Lee

[57] ABSTRACT

A process for the alkylation of secondary aliphatic amines is provided which consists of reacting a secondary aliphatic amine with at least one hydrogen on the alpha carbon atom of the amino group with an olefine in the presence of an amide of a transition metal.

4 Claims, No Drawings

PROCESS FOR THE ALKYLATION OF SECONDARY ALIPHATIC AMINES IN THE PRESENCE OF AN AMIDE OF A TRANSITION METAL

This invention relates to a process for the alkylation of secondary aliphatic amines, consisting of reacting a secondary aliphatic amine with at least one hydrogen on the alpha carbon atom of the amino group with a compound containing at least one olefinic unsaturation, in the presence of a particular type of catalyst.

Secondary aliphatic amines, tertiary aliphatic amines, particularly of long chain, and the quaternary ammonium salts easily obtainable therefrom are of notable importance. All these compounds are used as such mainly as surface active agents, some of which are biodegradable. They are also used in the textile industry as antistatic or softening agents, as wetting agents and as dye fixers. In the pharmaceutical industry they are used as bacteriostatic agents or bactericides, and as ganglionolithic agents. More generally, they may be used in the flotation of certain minerals, as additives for emulsifying asphalts and as oil additives in the form of corrosion inhibitors. They are used in the paint industry as pigment dispersing agents, and in certain cosmetic preparations as additives. The compounds in question are also widely used in the chemical industry as intermediates in the preparation of interesting derivatives. For example, secondary aliphatic amines are used in the synthesis of enamines, which on polymerization produce auxiliary products for the textile industry and for the production of plastics. This very wide range of applications thus makes secondary aliphatic amines and their derivatives of great interest. However, up to the present time there have been difficulties in their synthesis. Their synthesis from petroleum cuts gives rise to considerable disadvantages in addition to the need for multi-stage processes.

In this respect, methods are known for the alkylation of ammonia and amines, mainly at the expense of the nitrogen, these methods being essentially based on the use of heterogeneous catalytic systems (U.S. Pat. Nos. 2,381,473 and 2,623,061). Chain elongation at the expense of the carbon has also been carried out, but only by the use of peroxides which gives rise to the usual disadvantages related to this type of catalysis.

We have now discovered that it is possible to alkylate secondary aliphatic amines by the surprising use of metal catalysts and conducting the reaction in the homogeneous phase, this being most remarkable in that it is contrary to all knowledge up to the present time and absolutely unforseeable from prior teaching.

To this end, the present invention provides a process for the alkylation of secondary aliphatic amines comprising the reaction between a secondary aliphatic amine with at least one hydrogen on the alpha carbon atom of the amino group, and a compound containing at least one olefinic unsaturation, preferably an olefine itself, in the presence of a catalyst consisting of an amide of a transition metal, of formula $$M(NR_2)_n$$

in which R is alkyl, aryl or cycloalkyl, n is the valency of the metal and M is the metal itself, which as stated belongs to the transition metal series and is preferably chosen from Ti, Zr, Hf, V, Nb, Ta, Cr, Mo and W. The catalyst may be added to the reaction environment already formed, or may be obtained in situ by adding a salt of the transition metal to the amine concerned. It is evident that in this case the amido radical which becomes bonded to the metal derives from the secondary aliphatic amine which is to be alkylated.

The reaction takes place at a temperature of 100°–250° C. in the presence of an aprotic solvent. Toluene, xylene, glyma, diglyma, tetrahydrofuran, pyridine, and chloroform are particularly useful.

In the case of an alpha-olefine, the addition is of Markovnikow type. In the more general case, the reaction equation is as follows.

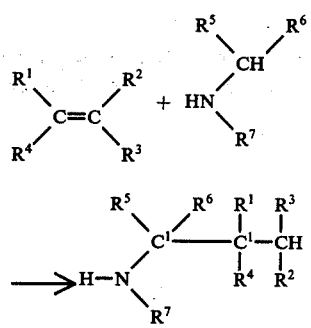

where the various R groups indicate hydrocarbon radicals.

The nature of the compounds obtained and further details of the operational conditions will be more evident from the illustrative examples given hereinafter which however in no way limit the invention.

EXAMPLE 1

50ml of anhydrous degasified toluene, one gram of Nb(Et$_2$N)$_4$ and 15ml of anhydrous Et$_2$NH are fed into a stainless steel reactor of capacity 400cc, and 10g of ethylene are added. The operations are carried out in an inert gas atmosphere.

Reaction is continued at 160° C. for 8 hours under magnetic agitation.

10g of ethyl sec-butylamine are obtained, and separated by distillation (boiling point = 98° C. at atmospheric pressure).

EXAMPLE 2

50ml of degasified anhydrous glyma, 1.2g of Ta(Me$_2$N)$_5$, 10g of anhydrous (CH$_3$)$_2$NH and 15g of propylene are fed into the same reactor as in example 1.

The mixture is reacted at 170° C. for 10 hours under agitation.

9.5g of methyl isobutylamine (N-methyl, N-2 methylpropylamine) are obtained, and separated by distillation (B.P. 78°).

EXAMPLE 3

50ml of anhydrous toluene, 1g of Nb(NMe$_2$)$_5$, 15g of pure 1-hexene and 10g of anhydrous (CH$_3$)$_2$NH are fed into the reactor described in the previous example. The mixture is reacted for 18 hours at 180° C. under agitation. 7.2g of (N-methyl, N-2 methylhexylamine) are obtained, and separated by extraction from the solution after evaporating the excess dimethylamine (acid-base extraction).

EXAMPLE 4

20g of 1-undecene and 10g of $(CH_3)_2NH$ are reacted in accordance with the method of example 3 with $Zr(Me_2N_4)$ (1g) in 50ml of toluene. After 20 hours at 200° C., (N-methyl, N-2 methylundecylamine) is obtained, and is separated by chromatography on an $Al_2O_3$ column.

EXAMPLE 5

15g of 1-hexene, 10g of $(CH_3)_2$ NH and 1.3g of $Ta(Me_2N_5)$ in 50ml of toluene are reacted under the same conditions as example 3 for 15 hours at 200° C., to give 7.3g of (N-methylhexylamine).

EXAMPLE 6

15g of 1-hexene, 10g of $(CH_3)_2NH$ and 0.9g of $NbCl_5$ in 50 ml of anhydrous toluene are reacted under the same conditions as example 3 for 24 hours at 200° C. to give 4.2g of N-methyl, N-2 methylhexylamine.

What we claim is:

1. A process for the alkylation of secondary aliphatic amines consisting of reacting a secondary aliphatic amine containing at least one hydrogen on an alpha carbon atom with an olefine in the presence of an amide of a transition metal.

2. A process as claimed in claim 1, wherein the reaction is carried out at a temperature variable from 100°–250° C.

3. A process as claimed in claim 2, wherein the reaction is carried out in the presence of an aprotic solvent.

4. A process as claimed in claim 3, wherein the transition metal is chosen from Ti, Zr, Hf, V, Nb, Ta, Cr, Mo and W.

* * * * *